United States Patent [19]

Kondo

[11] 4,075,336
[45] Feb. 21, 1978

[54] THIAZINES AND METHOD

[75] Inventor: Yasunori Kondo, Tokyo, Japan

[73] Assignee: Kanto Ishiseiyaku Co., Ltd., Tokorozawa, Japan

[21] Appl. No.: 745,762

[22] Filed: Nov. 29, 1976

[30] Foreign Application Priority Data

Mar. 11, 1976 Japan .................................. 51-26353

[51] Int. Cl.² .................... C07D 279/08; A61K 31/54
[52] U.S. Cl. ........................................ 424/246; 544/50
[58] Field of Search ..................... 260/243 R; 424/246

[56] References Cited

U.S. PATENT DOCUMENTS 3,257,396  6/1966  Koo ..................................... 260/244
3,455,915  7/1969  Krapcho ............................. 260/243

OTHER PUBLICATIONS

Bohme et al., Archiv der Pharmazie, vol. 286, pp. 330-7 (1953).

*Primary Examiner*—John M. Ford
*Attorney, Agent, or Firm*—Oblon, Fisher, Spivak, McClelland & Maier

[57] ABSTRACT 4-oxo-2-(3-hydroxy-4-methoxyphenyl)-2, 3-dihydro-5, 6-benzo-1, 3-thiazine and pharmaceutically acceptable salts thereof are provided. The thiazine is produced by a process which comprises reducing a dithiosalicyclic acid amide of the formula

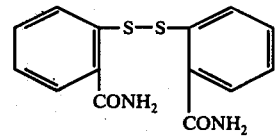

to form the thiosalicyclic acid amide of the formula

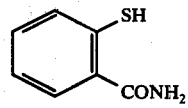

and reacting the resulting compound with isovanillin.

4 Claims, No Drawings

THIAZINES AND METHOD

BACKGROUND OF THE INVENTION

1. Field of the Invention

This invention relates to a novel thiazine derivative and a process for producing the same.

2. Description of the Prior Art

Hitherto, many anti-inflammatory and analgesic drugs have been known. However, often, these possess high toxicity relative to their effectiveness. Consequently, a need exists for less toxic, more effective anti-inflammatory and analgesic drugs.

SUMMARY OF THE INVENTION

Accordingly, it is an object of the present invention to provide a new compound possessing superior anti-inflammatory and analgesic effects with attendant low toxicity which is clinically effective.

It is another object of the present invention to provide a novel process for producing the new compound.

Briefly, these and other objects of this invention as will hereinafter become clear have been attained by providing 4-oxo-2-(3-hydroxy-4-methoxyphenyl)-2, 3-dihydro-5, 6-benzo-1, 3-thiazine, represented by the formula:

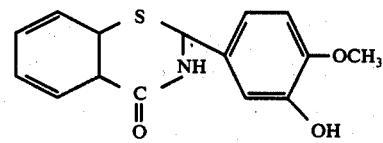

(I)

and pharmaceutically acceptable salts thereof.

Compound (I) may be produced in accordance with this invention by reducing the dithiosalicylic acid amide (II) to form the thiosalicylic acid amide (III), and reacting the resulting compound with isovanillin (IV), as shown by the following reaction scheme:

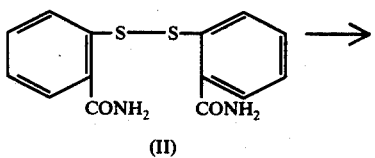

(II)

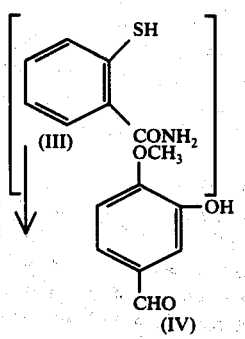

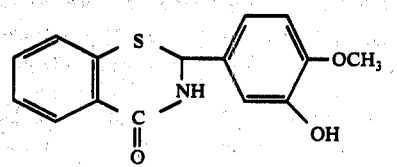

(I)

DETAILED DESCRIPTION OF THE PREFERRED EMBODIMENTS

The starting material (II) is a known compound. It can be easily produced by reacting thiosalicyclic acid with ferric chloride and concentrated hydrochloric acid with application of heat to form dithiosalicyclic acid. The resulting compound can be halogenated to form dithiosalicylic acid halogenide, and the halogenide then reacted with ammonia.

The process of this invention may be performed as follows.

The conventional reduction methods for conversion of dithiocompounds into thiolcompounds are suitable for use in the reduction of the dithiosalicylic acid amide (II). For instance, the dithiosalicylic acid amide (II) can be dissolved in an inert solvent such as dioxane and the like and the resulting mixture reacted with zinc-hydrochloric acid for several hours to produce the thiosalicylic acid amide (III). Since the product thiosalicylic acid amide (III) is subject to immediate oxidation in air to reform the dimer, the above reaction mixture should be extracted with ethyl acetate or a similar organic extracting medium, i.e., organic solvent, and the extract freed of the solvent and submitted to the next reaction step without further purification.

The reaction of the thiosalicylic acid amide (III) with isovanillin (IV) is preferably conducted in an inert solvent such as ethanol, benzene or the like, at 40° – 70° C for 0.5 – 1.5 hours. This reaction is further preferably conducted while bubbling carbon dioxide and dry HCl gas into the reaction chamber and also while removing the water formed during the reaction. Preferably, 2 to 3 moles of isovanillin (IV) are used per mole of dithiosalicylic acid amide (II).

The thiazine derivative (I) of the present invention has been found to possess superior anti-inflammatory and analgesic effects, while possessing lower toxicity and extreme clinical effectiveness. These properties are shown below in comparison with those of methiazinic acid [α-(10-methyl-2-pheno-thiazinyl)-acetic acid], which is known as an excellent anti-inflammatory and analgesic drug [Oyoyakuri, 6, No. 6, pp1457–1478 (1972)].

A. Acute toxicity

Animals [dd strain mice; 5 groups of males and 5 groups of females, each group consisting of 8 animals] were intraperitoneally given the compound of this invention in doses of 2000, 2400, 2880, 3456 and 5000 mg/kg. In both the male and female groups, no deaths were observed. Based on this finding, it may be concluded that the value of $LD_{50}$ is at least more than 5000 mg/kg.

Accordingly, the toxicity of the compound of this invention is less than one/tenth that of methiazinic acid, because the value of $LD_{50}$ of the latter compound is about 500 mg/kg.

B. Analgesic effect (Randall-Selitto method)

Using an analgesic effect measuring apparatus (made by Ugo Basile Co., Ltd.), pain thresholds in rats were measured as a function of elapsed time and compared with normal pain threshold values which had previously been determined. Each group consisted of 5 animals, which were subcutaneously given 0.1 ml of a 1% carrageenan suspension on their right paws. The test compounds were given orally, 1 hour before the carrageenan medication. The experiments were repeated twice under the same conditions. The mean values of the results obtained for 10 animals were compared with those of methiazinic acid.

The results obtained are shown in Table 1, wherein "OS" refers to oral administration.

Table 1.

| Drug | Dosage mg/Kg per os | Number of animals | Paws | Pain threshold (mm Hg) | | | | | | | Analgesic coefficient |
|---|---|---|---|---|---|---|---|---|---|---|---|
| | | | | Before medication | After 30 min. | After 60 min. | After 90 min. | After 120 min. | After 180 min. | After 240 min. | |
| Saline solution | — | 10 | Normal | 65.8 | 64.8 | 61.8 | 58.5 | 58.6 | 59.0 | 58.8 | 0.92 |
| | | | Inflammated | 65.5 | 56.2 | 47.8 | 40.7 | 35.7 | 26.4 | 35.2 | 0.62 |
| Methiazinic acid | 50 | 10 | Normal | 67.2 | 66.2 | 65.3 | 63.8 | 62.0 | 59.7 | 61.3 | 0.94 |
| | | | Inflammated | 66.8 | 62.7 | 57.7 | 48.9 | 43.5 | 39.0 | 44.5 | 0.74 |
| Methiazinic acid | 100 | 10 | Normal | 66.9 | 69.0 | 66.7 | 65.5 | 64.8 | 62.8 | 64.0 | 0.98 |
| | | | Inflammated | 67.7 | 69.3 | 66.7 | 57.3 | 49.5 | 47.2 | 47.2 | 0.83 |
| Compound of this invention | 50 | 10 | Normal | 67.3 | 66.7 | 66.0 | 64.0 | 61.7 | 57.3 | 60.8 | 0.93 |
| | | | Inflammated | 66.8 | 62.5 | 57.7 | 48.0 | 41.8 | 36.8 | 44.2 | 0.73 |
| Compound of this invention | 100 | 10 | Normal | 66.0 | 65.0 | 65.7 | 65.2 | 62.5 | 61.0 | 61.2 | 0.96 |
| | | | Inflammated | 65.6 | 66.7 | 63.7 | 57.2 | 49.0 | 43.3 | 43.2 | 0.82 |

As can be seen from the results in Table 1, the compound of this invention clearly exerts analgesic effects in doses of 50 and 100 mg/kg. As shown by the comparison with the pain threshold value of methiazinic acid with elapsed time, the present compound shows about the same duration and strength of effect as methiazinic acid.

C. Anti-inflammatory effect (Carrageenen-induced edema)

Wister-strain rats (each group consisting of 5 animals) were subcutaneously given 0.1 ml of a 1% carrageenan suspension on their right paws. The volumes of the right paws were measured prior to the administration, and thereafter were measured with elapsed time. The inhibitory percent was calculated, in comparison with a control, on the basis of the volume of edema induced. The volume was estimated with reference to the volume before the carrageenan-injection. The test compounds were orally administered 1 hour before the carrageenan-injection. The same experiments were repeated twice. The mean values of the results in all 10 animals were compared with those of methiazinic acid. The results are shown in Tables 2 and 3.

Table 2.

| | Inhibitory effect in carrageenan-induced edema | | | | | | |
|---|---|---|---|---|---|---|---|
| Drug | Dose mg/kg per os | Number of animals | edema percent (inhibitory percent) | | | | |
| | | | 1 hr. | 2 hrs. | 3 hrs. | 4 hrs. | 5 hrs. |
| Saline solution | — | 10 | 48.3 | 64.1 | 68.9 | 62.4 | 58.7 |
| Methiazinic acid | 50 | 10 | 38.8 (19.6) | 47.7 (25.5) | 48.8 (29.2) | 46.7 (25.2) | 39.4 (32.9) |
| Present compound | 50 | 10 | 29.3 (39.2) | 43.1 (32.6) | 43.1 (37.3) | 42.4 (32.1) | 37.4 (36.4) |

Table 3.

| | Inhibitory effect in carrageenan-induced edema | | | | | | |
|---|---|---|---|---|---|---|---|
| Drug | Dose mg/kg per os | Number of animals | edema percent (inhibitory percent) | | | | |
| | | | 1 hr. | 2 hrs. | 3 hrs. | 4 hrs. | 5 hrs. |
| Saline solution | — | 10 | 41.6 | 62.7 | 69.7 | 64.6 | 58.3 |
| Methiazinic acid | 100 | 10 | 34.2 (17.7) | 38.1 (39.3) | 40.1 (42.4) | 39.7 (38.5) | 36.0 (38.3) |
| Present compound | 100 | 10 | 24.1 (42.1) | 31.5 (49.9) | 34.6 (50.4) | 33.9 (47.5) | 35.5 (39.1) |

As can be seen from the results of Tables 2 and 3, the anti-inflammatory effect of the compound of this invention exerts a significant effect 1 hour after administration. It also exerts a long duration effect, which was observed even after 5 hours. This effect is very similar to that of methiazinic acid.

Having generally described the invention, a further understanding can be obtained by reference to certain specific Examples which are provided herein for purposes of illustration only and are not intended to be construed as limiting unless otherwise specified.

EXAMPLE 1

4 g (0.013 mole) of dithiosalicylic acid amide was dissolved in dioxane. To the resulting mixture was added 2.4 g (0.037 mole) of zinc. 40 ml of 2N-hydrochloric acid was then added dropwise with stirring. The resulting mixture was heated on a water bath for 6 hours. After the completion of the reaction, the mixture was cooled and extracted with ethyl acetate. The extract was washed with 10% potassium bicarbonate and then with a saturated sodium chloride solution. The solvent was evaporated under reduced pressure to obtain oily thiosalicylic acid amide. Since this compound showed a tendency toward oxidation to the dimer, it was submitted to the next reaction step without purification and crystallization.

The thiosalicylic acid amide obtained and 4 g (0.026 mole) of isovanillin were dissolved in anhydrous ethanol, while carbon dioxide and dry HCl gas were bubbled into the reaction chamber. Thereafter, dry benzene was added to the mixture, and water was distilled off as an azeotrope. The mixture was heated on a bath at 60° - 70° C with stirring for 1 hour, while carbon dioxide and dry HCl gas where bubbled into the mixture. After cooling, the separated crystals were collected by filtration and washed with 50% ethanol.

After drying, these crystals were recrystallized from ethanol to yield 3.5 g (yield 46.7%) of 4-oxo-2-(3-hydroxy-4-methoxyphenyl)-2, 3-dihydro-5, 6-benzo-1, 3-thiazine having a melting point of 228° - 232° C.

The properties of this compound are as follows

| Elemental Analysis: | C | H | N |
|---|---|---|---|
| Measured (%): | 62.71 | 4.52 | 4.87 |
| Calculated (%): | 62.58 | 4.65 | 4.63 |

MS (Shimadzu Model LKB-9000)
  m/e 287 (M$^+$)
  m/e 264
  m/e 151
  m/e 137
  m/e 136
  m/e 91
  m/e 84

UV (Shimadzu Model DOVBLE 40R)
  $\lambda_{max}^{MeOH}$ 230 nm ($\epsilon$=3592), 252 nm ($\epsilon$=2080.5)

IR (Nippon Bunko Tasco IR-G)
  3210, 3160 cm$^{-1}$ (NH,OH)
  1652 cm$^{-1}$ (C=O)

NMR (Hitachi Model R-22)
  $\delta$: (in $d_6$ — DMSO)
    3.72, 5.95, 5.96, 7.10 – 7.58, 7.96, 8.80, 9.06
  Peaks at $\delta$ values of 8.80 and 9.06 disappeared by adding $D_2O$

Having now fully described the invention, it will be apparrent to one of ordinary skill in the art that many changes and modifications can be made thereto without departing from the spirit or scope of the invention as set forth herein.

What is claimed as new and desired to be secured by letters patent of the United States is:

1. 4-oxo-2-(3-hydroxy-4-methoxyphenyl)-2, 3-dihydro-5, 6-benzo-1, 3 -thiazine and pharmaceutically acceptable salts thereof.

2. A method for decreasing inflammation in mammals which comprises administering an anti-inflammatory effect amount of the compound of claim 1.

3. A method of reducing pain in animals which comprises administering an analgesic effective amount of the compound of claim 1.

4. A pharmaceutically effective composition which comprises a pharmaceutically effective amount of the compound of claim 1 and a pharmaceutically acceptable adjrevant.

* * * * *